(12) United States Patent
Matos

(10) Patent No.: US 12,246,498 B2
(45) Date of Patent: Mar. 11, 2025

(54) PATIENT SPECIFIC SYSTEM AND METHOD TO REPAIR AORTIC ANEURYSMS

(71) Applicant: Gabor Matos, Springfield, IL (US)

(72) Inventor: Gabor Matos, Springfield, IL (US)

(*) Notice: Subject to any disclaimer, the term of this patent is extended or adjusted under 35 U.S.C. 154(b) by 407 days.

(21) Appl. No.: 17/359,549

(22) Filed: Jun. 26, 2021

(65) Prior Publication Data
US 2022/0410513 A1 Dec. 29, 2022

(51) Int. Cl.
| | |
|---|---|
| B29D 23/00 | (2006.01) |
| A61B 8/13 | (2006.01) |
| A61F 2/06 | (2013.01) |
| A61F 2/07 | (2013.01) |
| A61L 27/50 | (2006.01) |
| A61M 25/10 | (2013.01) |
| B33Y 10/00 | (2015.01) |
| B33Y 80/00 | (2015.01) |

(52) U.S. Cl.
CPC .............. *B29D 23/00* (2013.01); *A61B 8/13* (2013.01); *A61F 2/06* (2013.01); *A61F 2/07* (2013.01); *A61L 27/507* (2013.01); *A61M 25/1027* (2013.01); *B33Y 80/00* (2014.12); *A61F 2002/065* (2013.01); *A61F 2240/004* (2013.01); *A61F 2250/0003* (2013.01); *A61L 2420/02* (2013.01); *B33Y 10/00* (2014.12)

(58) Field of Classification Search
None
See application file for complete search history.

(56) References Cited

U.S. PATENT DOCUMENTS

| | | | | |
|---|---|---|---|---|
| 5,330,528 | A * | 7/1994 | Lazim | A61F 2/07 623/1.25 |
| 5,628,783 | A * | 5/1997 | Quiachon | A61F 2/954 623/1.35 |
| 2006/0025853 | A1* | 2/2006 | Evans | A61F 2/07 623/1.21 |
| 2007/0207182 | A1* | 9/2007 | Weber | A61L 29/12 607/2 |
| 2007/0279435 | A1* | 12/2007 | Ng | G06F 3/04815 345/624 |
| 2009/0112305 | A1* | 4/2009 | Goldmann | A61F 2/07 623/1.42 |
| 2016/0310303 | A1* | 10/2016 | Thapliyal | A61F 2/856 |
| 2017/0239035 | A1* | 8/2017 | Schreck | A61F 2/07 |
| 2018/0245243 | A1* | 8/2018 | Krieger | B29C 33/485 |

* cited by examiner

*Primary Examiner* — Leslie A Lopez (57) ABSTRACT

This invention addresses the need of repairing aortic aneurysms. The method embodies the manufacturing of patient and anatomy specific endovascular implant. Additional advantages of the invention relate to smaller delivery size, improving the risk of graft migration and endoleak formation.

13 Claims, 5 Drawing Sheets

PATIENT SPECIFIC SYSTEM AND METHOD TO REPAIR AORTIC ANEURYSMS

BACKGROUND

Field of the Invention

The present invention relates to the treatment of aneurysms, and in particular, a system for repairing aortic aneurysms.

Description of the Related Art

The demographic changes in the developed world demonstrate significant aging of the population. In 2013, 13.5% of the population aged over 65, a statistic which is expected to increase to 20.2% by 2050. The advancing age of the population results in marked incidence of certain diseases, including aortic aneurysms. The estimated prevalence of abdominal aortic aneurysm in mend older than 65 years of age is 4.7%. Rupture of the aortic aneurysm occurs in 1-3% of men aged 65 or more and the mortality rate is 70-95%.

An aneurysm occurs when an arterial wall becomes wakened to the extent that the weakened section balloons under pressure from the blood flowing through the artery. An aneurysm can lead to fatality if it ruptures causing rapid loss of blood.

Currently available screening technology enables physicians to capture most aneurysms if the guidelines for screening are appropriately implemented. Well established data confirms that repair of the aneurysm prevents rupture and death. Repair is indicated when the maximal diameter of the aneurysm exceeds 5.5 cm and/or the growth rate exceed 0.5 cm per year.

One option for repairing an aortic aneurysm is open surgical repair. This is an extensive procedure associated with significant mortality, approximately 3-5% at 30 days, and morbidity. Another option for repair is an endovascular repair procedure wherein an implant is inserted into the aneurysm via the femoral artery to take the blood flow and to isolate the aneurysm. The implant can include a graft. Some implants are in the shape of a tube. Some implants incorporate a stent. Some grafts incorporate a bifurcation to accommodate the bifurcation in the abdominal aorta when it reaches the iliac arteries. Endovascular repair lowers the 30 day mortality rate to 0.5%. In addition, endovascular repair only requires secondary vascular procedures 33% of the time.

Many patients do not qualify for endovascular repair because of anatomical factors related to the size and stiffness of the implant and delivery system. Some conditions which preclude safe placement of an implant include a short aneurysm neck (<15 mm), angulation of the aorta, tortuosity, extensive thrombus in the proximal segment, and diseased and/or small caliber common femoral and iliac arteries. Some recent advancements which attempt to address some of these issues include: shrinking the size of the implant, employing supra-renal and transaortic fixation to prevent migration of the implant, "snorkel" side branches, and embolizing other branches.

An additional problem with existing implants is that over time, the graft can slip due to the effect of pulsatile blood flow through the implant as well as changes in the morphology of the arteries. Over time the integrity of the implant and isolation of the aneurysm can be compromised.

SUMMARY

The systems, methods and devices described herein have innovative aspects, no single one of which is indispensable or solely responsible for their desirable attributes. Without limiting the scope of the claims, some of the advantageous features will now be summarized.

One aspect of the present invention is the realization that conventional systems for the treatment of aortic aneurysms require additional fixation features to prevent migration, require snorkeling or embolization of side branches, and exclude patients with small caliber or diseased femoral or iliac arteries. Thus, there exists need for an improved system for repair of aortic aneurysms.

One non-limiting embodiment of the present invention includes a system for the repair or aortic aneurysms.

Another non-limiting embodiment of the present invention includes a method of manufacturing the invention described herein, including one or more of the steps of performing an computer tomography angiography on a patient having an aneurysm; processing images related to the angiography into software format enabling 3 dimensional printing, I.e. digital imaging communications in medicine (DICOM); and producing a custom patient-specific aneurysm endovascular implant, i.e. endograft, based on the angiographic images. In some embodiments, the custom patient-specific aneurysm endograft can be manufactured using a 3D printer.

Another non-limiting embodiment of the present invention includes a method of use of the invention described herein.

In some embodiments, disclosed herein is a patient-specific endograft, comprising an outer wall configured when in a fully expanded state to substantially take the shape of an aneurysmal wall of a patient; an inner wall configured to conduct arterial blood flow therethrough; and a cavity between the outer wall and the inner wall configured to hold a filler material within the cavity. The implant can be configured to be placed within the abdominal aortic aneurysm of a patient. At least a portion of a first wall, such as the inner wall, can be coated with a therapeutic agent, such as an anticoagulant. At least a portion of a second wall, such as an outer wall, can be coated with a hemostatic agent.

Also disclosed herein is a method of manufacturing an endograft, comprising one or more of the steps of receiving image data relating to a computer tomography angiographic (CT angiography) procedure of a patient, the patient having an aneurysm; processing images relating to the angiographic procedure; and producing a custom-patient specific endovascular implant based upon the image data, wherein the endovascular implant comprises an outer wall configured when in a fully expanded state to substantially take the shape of the aneurysm of the patient.

In some embodiments, producing a custom-patient specific endovascular implant comprises utilizing a 3D printer to manufacture mandrels used for injection or blow molding of the walls of the endograft.

Both mandrels are printed from a heat resistant material, which can be subjected to molding process used in standard balloon manufacturing techniques; the mandrels are printed in a format (positive or negative) to accommodate the planned balloon manufacturing technique including but not exclusive of injection molding, blow molding and dip molding;

In case of porosity or irregularity of the surface of the mandrels, as the result of 3 D printing, post printing surface modification is performed, including but not exclusive of polishing and coating with heat resistant sealer.

Using both mandrels and appropriate balloon manufacturing technique the inner and outer walls of the endograft are produced.

The inner wall is manufactured from a non-compliant material including but not exclusive of nylon or polyester using techniques including but not exclusive of injection and or blow molding;

The outer wall is manufactured from a compliant material so it can better accommodate the irregular shape of the native aneurysm wall; These material include without exclusivity silicone and polyurethane; The balloon manufacturing technique includes dip molding, blow molding or injection molding.

Filling tube is attached to the outer wall of the endograft, to enable filling the space between the inner and outer walls of the endograft resulting in full deployment of the endograft; the filling tube is detachable in its mid section into a proximal and distal part;

A thin plastic flap covering the entry point of the filling tube into the endograft cavity, wherein the flap serves as a one way valve to prevent back flow of the filling material from the endograft cavity into the filling tube.

An additional one way valve is added into the filling tube for additional security in preventing back flow.

The filling tube is detachable distal to the said one way valve to allow removal after injecting the filling material.

The inner and outer walls of the endograft are attached and safely secured together with an absolutely watertight technology at the proximal and distal ends thus creating a watertight cavity between the walls.

The endograft is tested for complete sealing and all potential leak is eliminated.

The inner surface of the inner wall is coated with an anticoagulant, such as Heparin, to minimize the risk of blood clotting within the endograft;

The outer surface of the outer wall is coated with a procoagulant, such as Thrombin, to promote closure of side branches, such as lumbar arteries, thus minimizing the possibility of the development of endoleak.

All surfaces of the endograft are sterilized.

The endograft is folded into a delivery catheter, wherein the delivery catheter has a 0.035" inner lumen to accommodate a stiff guide wire and an outer sheath which contains the folded endograft and once in position within the lumen of the aorta, the outer sheath is pulled back and out of the body to allow for inflation of the cavity of the endograft.

The filling of the cavity between the inner and outer walls of the endograft is comprised of the following steps:

Injecting the first component of the filling material inflates the endograft and self-positions the device within the body of the aneurysm, said first component is liquid thus allows for deflation and repositioning if necessary, Once perfect positioning is achieved, the second component is injected which induces a chemical reaction resulting in solidification of the filler into a semi rigid state, said semi rigid state maintains the shape of the endograft thus securing its position within the aneurysm but allows for minimal deformation to accommodate natural movement of the vasculature during daily life as well as for the changing shape of the native aneurysm with time Following the completion of the filling process, the distal part of the filling tube is removed the proximal part remains trapped between the aorta and the endograft and the guide wire is removed.

System comprising CT scanner, 3D printer, polymer molding machinery and computers using proprietary software to conduct the above mentioned operation.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Figure 1:
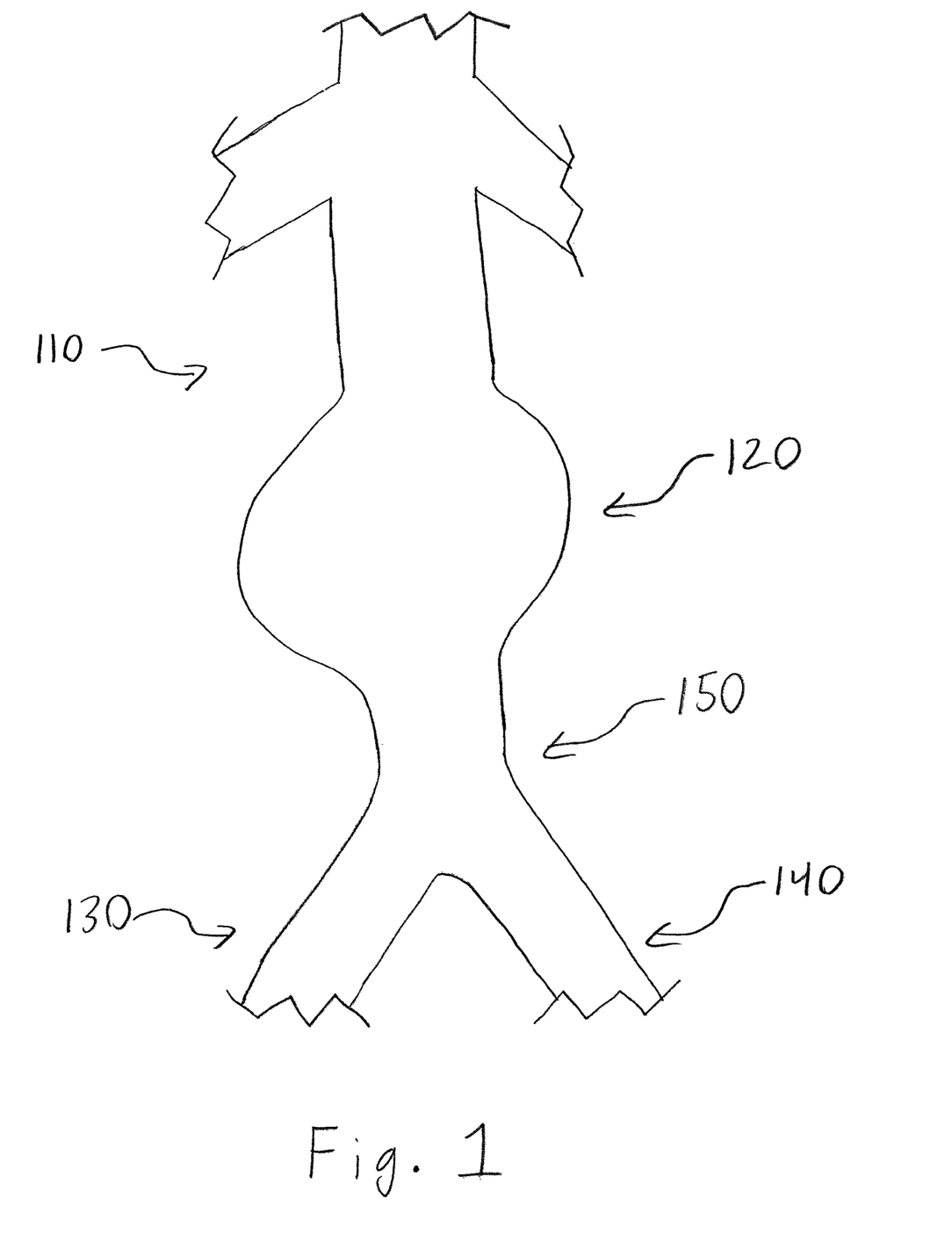
FIG. 1 illustrates a cross section of an abdominal aorta including an aneurysm.

FIG. 1 illustrates a cross section of an abdominal aorta 110 including an aneurysm 120. The aneurysm 120 is an expanded section of the aorta 110 which ballooned under pressure from the blood flowing through the artery. The aorta 110 feeds into the common iliac artery 130 and the contralateral common iliac artery 140 at the bifurcation 150.

Figure 2:
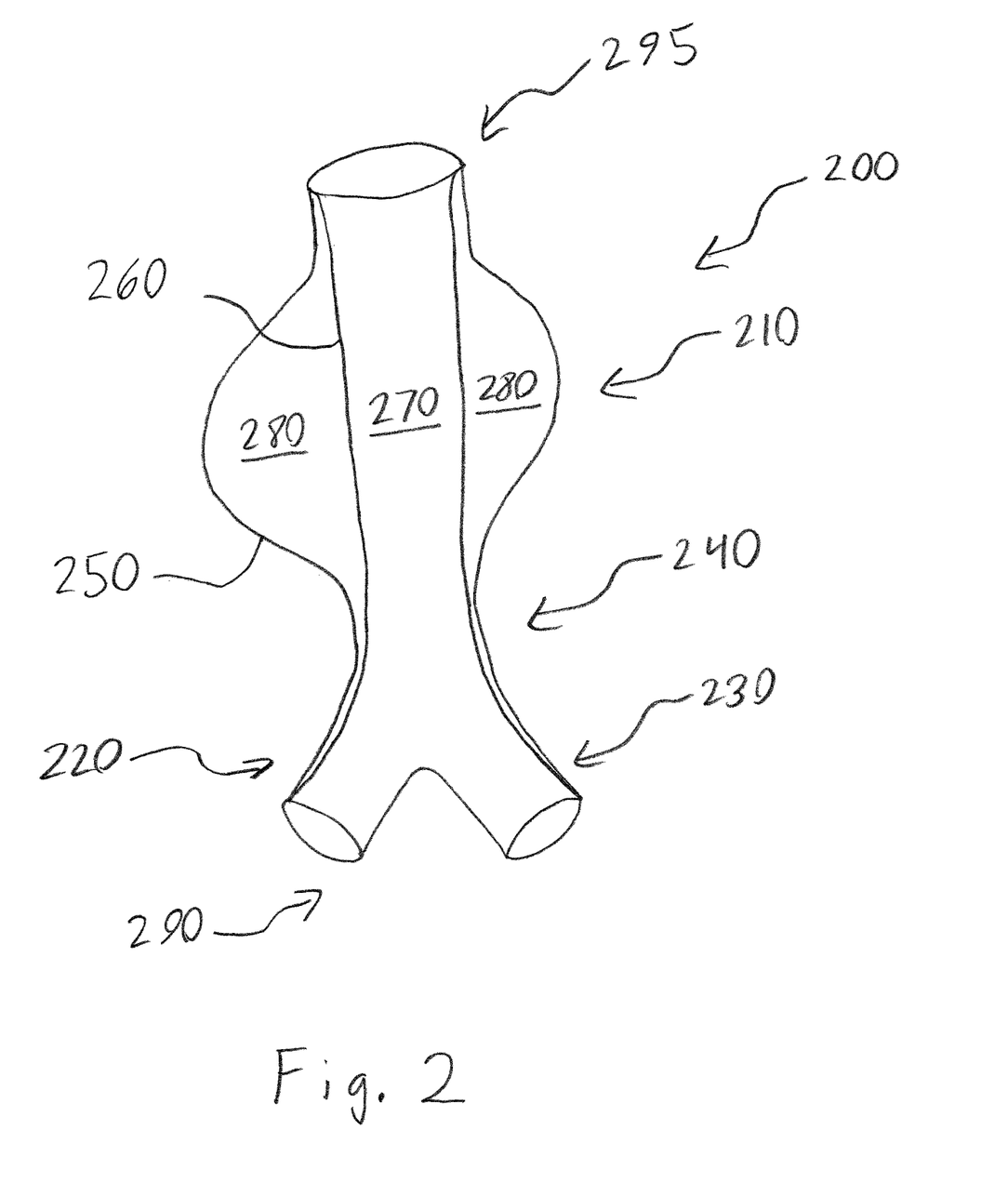
FIG. 2 illustrates a cross section of one embodiment of an implant for the repair of an arterial aneurysm.

FIG. 2 illustrates a cross section of one embodiment of an implant 200 for the repair of an arterial aneurysm 120. In some embodiments, the implant 200 can be used to repair an aneurysm 120 within the aorta 110. In some embodiments, the implant 200 can be a tubular graft. Due to the unique anatomy of every patient, a generic implant may not be effective at successfully repairing all aneurysms 120. In some embodiments, a custom implant 200 can be created for each patient and their unique anatomy and indications. Angiography, including fluoroscopic, computed tomographic (CT), and/or magnetic resonance (MR) angiography, for example, can be utilized to obtain images of a patient's aneurysm 120 and surrounding arterial network. The angiograms can then be used to determine the exact or substantially the exact size, configuration, and design of implant 200 necessary to repair the aneurysm 120. In some embodiments, software utilizes inputs such as the angiogram images to design an implant 200 in the exact or substantially exact shape implant required to repair the aneurysm 120. In some embodiments, each implant 200 can be created using a three dimensional stereo lithography printer, allowing each implant 200 to be constructed to match the anatomy of the patient. The implant 200 can be created using biocompatible materials which may include, for example, polyvinyl chloride (PVC), polypropylene, polyester such as polyglycolic acid (PGA), polylactic acid (PLA), poly(lactidelglycolide), polycaprolactone, polytetrafluoroethylene (PTFE), expanded PTFE (ePTFE), polyethylene, polyurethane, polyamide, nylon, polyetheretherketone (PEEK), polysulfone, a cellulose and its derivatives, fiberglass, an acrylic, polyvinyl alcohol, carbon, ceramic, a metal, polydioxanone, polyoxalate, a polyanhydride, a poly(phosphoester), catgut suture, collagen, silk, chitin, chitosan, hydroxyapatite, bioabsorbable calcium phosphate, hyaluronic acid, elastin, and combinations thereof, or any other materials capable of construction via three dimensional printing. In some embodiments, the custom-made nature of the implant 200 allow it to accommodate the specific anatomical idiosyncrasies of each individual patient, including thrombus burden, angulation, tortuosity, and need for preservation of side branches. In some embodiments, the implant 200 preserves the normal anatomy of the iliac bifurcation 150, allowing later vascular procedures on the legs via contralateral access. In some embodiments, the implant 200 can also include one, two, or more side branches, such as renal artery side branches for example, included in the implant's construction as necessary for the patient's anatomy.

In some embodiments, as illustrated in FIG. 2, the implant 200 can include an inner wall 260 and an outer wall 250. The outer wall 250 can be configured, when in a fully expanded configuration for example, to form the exact or substantially exact shape of the patient's native arteries, including the aneurysm 120, and/or any plaguing or irregularities therein. The inner wall 260 can be configured to form the normal shape of the vascular bed and provide a lumen 270 formed therein through which blood can flow. The inner wall 260 and the outer wall 250 form a filler pocket 280. In some embodiments, the implant 200 can include more than one filler pocket 280. In some embodiments, the filler pocket 280 is configured to accept a filler material. Filler material can be added to the filler pocket 280 such as via one or more ports (not shown) which may contain a valve in some embodiments, expanding the outer wall 250 until it meets and conforms to the arterial wall. The delivery catheter may have one or more exit ports configured to removably attach to one or more of the filler pocket ports. The filler material can help support the structure of the implant 200 while filling the void created by the aneurysm 120. In some embodiments, the filler material can include a first component which can be solidified upon an additional trigger once the implant is in position. In some embodiments, the first component is initially in a liquid form. In some embodiments an additional trigger could include, for example, a second component mixed with the first part, light, electrical stimulus, etc. In some embodiments, the filler can include biocompatible materials, which may include for example, a polymerizable material such as N-Butyl-cyanoacrylate or N-isopropyl acrylamide, collagen, hydrogel, a combination thereof, etc.

In some embodiments, the implant 200 is configured to be implanted in the aorta. In some embodiments, the implant 200 is configured to be implanted in the aortic arch. In some embodiments, the implant 200 is configured to be implanted in the thoracic aorta. In some embodiments, the implant 200 is configured to be implanted in the abdominal aorta 110. In some embodiments, the implant 200 is configured to be implanted partially in the abdominal aorta 110 and partially in at least one common iliac artery. In some embodiments, the implant 200 is configured to be implanted partially in the abdominal aorta 110 and partially in the common iliac artery 130 and the contralateral common iliac artery 140 as illustrated in FIG. 2. In some embodiments, the implant 200 can include an aortic portion 210, and at least one iliac portion. In some embodiments, as illustrated in FIG. 2, the implant can include an aortic portion 210, an iliac portion 220, and a contralateral iliac portion 230, wherein the aortic portion 210 is separated from the iliac portion 220 and contralateral iliac portion 230 by the bifurcation region 240. In some embodiments, the implant need not have a bifurcated inner wall portion as shown but rather could have a single stem straight or tapered endograft.

In some embodiments, the implant 200 does not require additional fixation to keep the implant 200 from migrating, but fixation could be enhanced by distal, proximal, or in between barbs, hooks, or other anchors. In some embodiments, the filler pocket 280 is filled with filler material and lodged in the aneurysm 120 of the artery, which can prevent the implant from migrating, and prevent buckling, migration, and/or leaking. In some embodiments, the bifurcation region 240 of the implant 200 also helps to prevent migration of the implant 200 as it interacts with the bifurcation 150 of the arteries.

In some embodiments, as illustrated in FIG. 2, the implant 200 can include a first end 290 and a second end 295. In FIG. 2, the first end 290 corresponds to the end of the iliac portion 220 and contralateral iliac portion 230 of the implant 200 and the second end 295 corresponds to the end of the aortic portion 210 of the implant 200. In some embodiments, the first end 290 and second end 295 of the implant 200 are configured to expand against the arterial wall and seal the implant 200 to the arterial wall, not allowing blood to flow outside of the lumen 270 of the implant 200. In some embodiments, portions of the implant 200, such as the inner wall 260 or the outer wall 250, can include a reinforcing structure, which may include for example, hoops, cages, or mesh.

Figure 3:
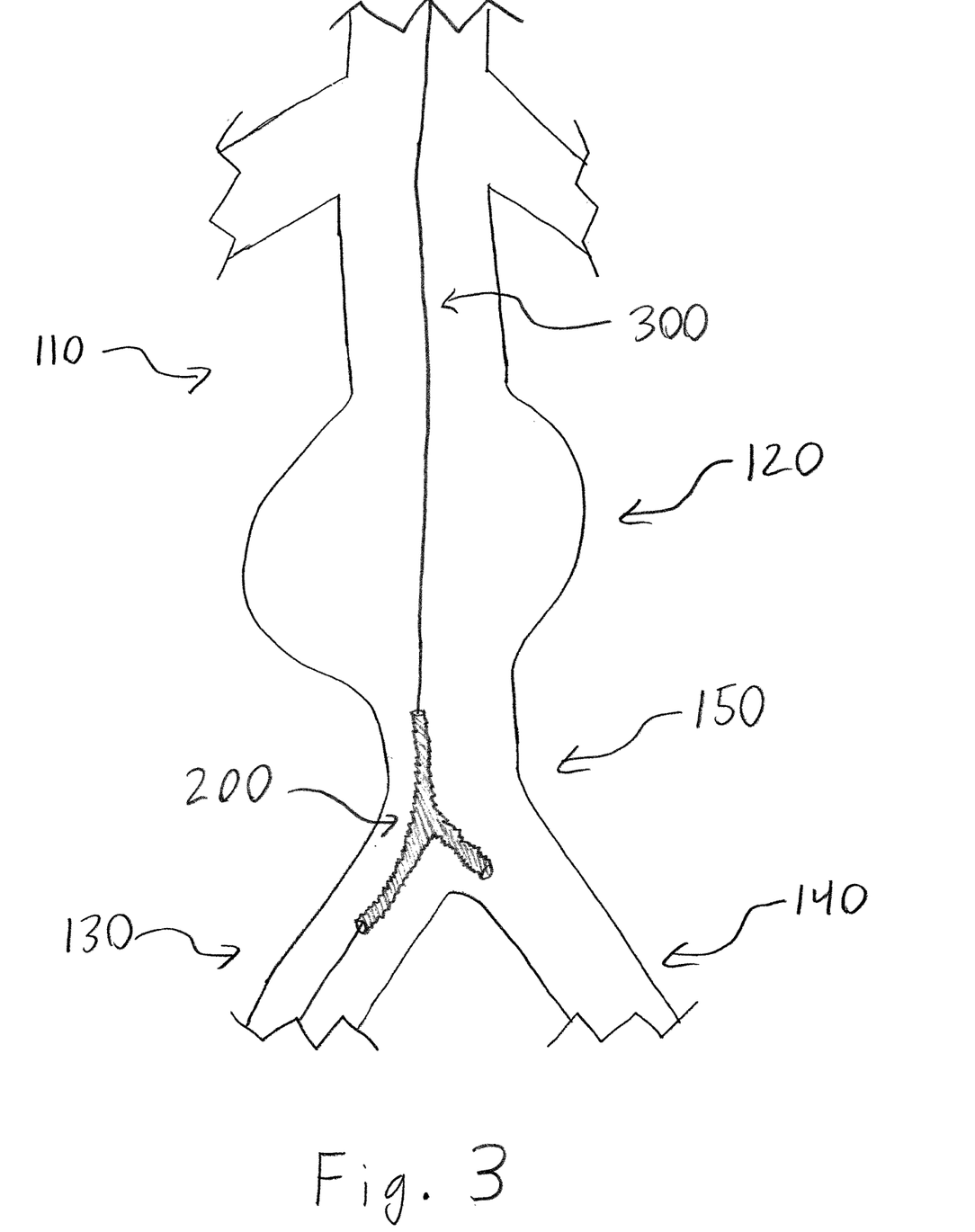
FIG. 3 illustrates a cross section of the implant of FIG. 2 being deployed into an abdominal aorta including an aneurysm.

FIG. 3 illustrates a cross section of the implant 200 of FIG. 2 being deployed into an abdominal aorta 110 including an aneurysm 120. In some embodiments, the implant 200 can utilize a delivery instrument 300 to deliver the implant 200 to the aneurysm 120. In some embodiments, the delivery instrument 300 can include a catheter. In some embodiments, the delivery instrument 300 can include a guide wire. In some embodiments, the implant 200 can be implanted through an endovascular approach through a femoral artery. In some embodiments, the implant 200 can be configured for easy and precise placement of the implant 200 through a small caliber sheath entirely percutaneously without need for surgical cut down or use of complex arterial closure devices. In some embodiments, before deployment, the implant 200 is folded so that it can be delivered within a catheter through the arteries to the aneurysm 120. In some embodiments, the implant 200 can be folded to fit within a 7 or 8 French (Fr) catheter and positioned in the required position, as illustrated in FIG. 3. In some embodiments, the implant 200 utilizes a two part delivery sheath. In some embodiments, at least a portion of the sheath is removed allowing the contralateral iliac portion 230 of the implant 200 to separate from the iliac portion 220 of the implant 200 as illustrated in FIG. 3.

Figure 4:
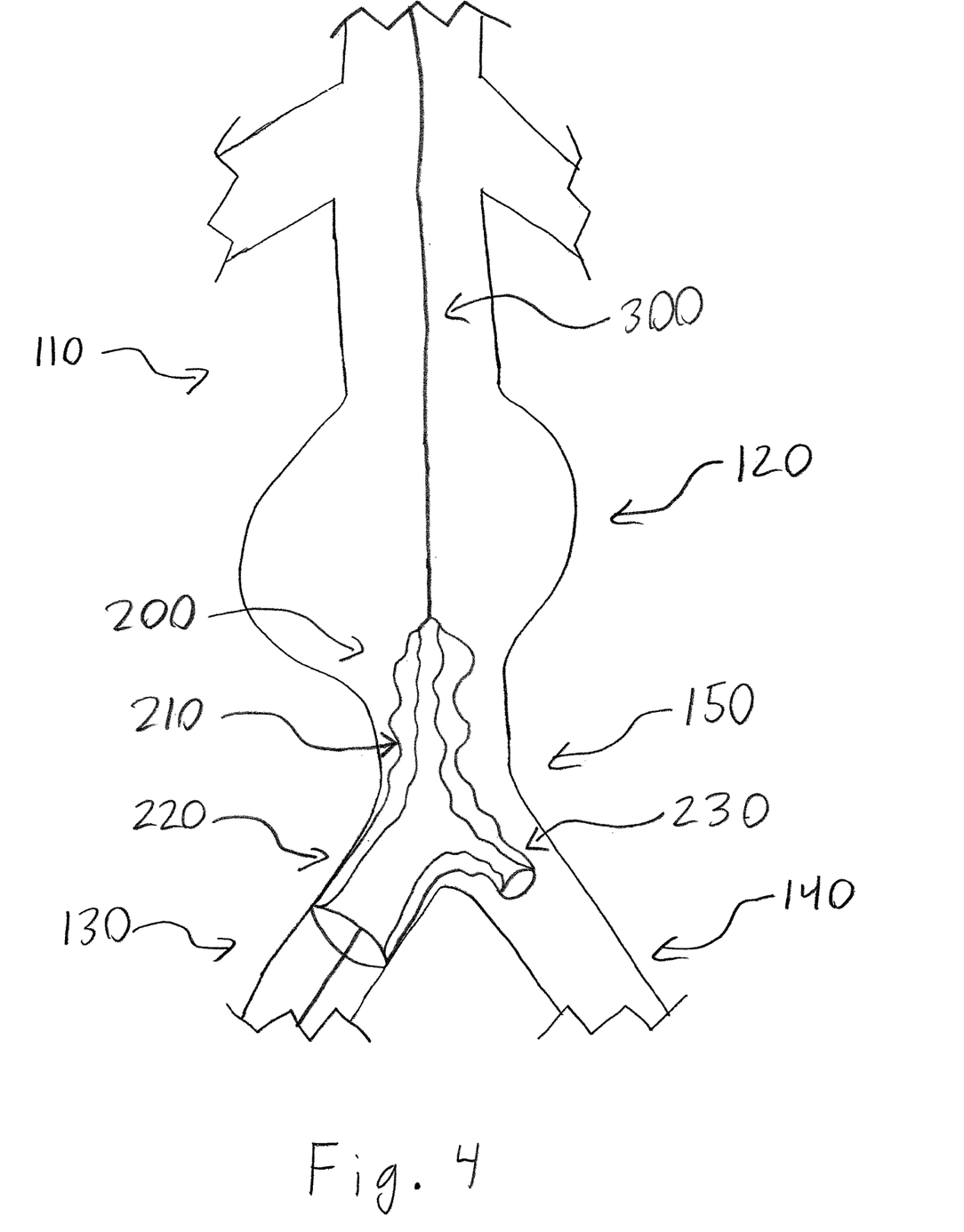
FIG. 4 illustrates a cross section of the implant of FIG. 2 being positioned into an abdominal aorta including an aneurysm. In some embodiments, implant is then partially filled with filler material.

FIG. 4 illustrates a cross section of the implant 200 of FIG. 2 being positioned into an abdominal aorta 110 including an aneurysm 120. In some embodiments, the filler pocket 280 of the implant 200 is then partially filled with filler material. This will cause the implant 200 to start to assume its shape, as illustrated in FIG. 4. Then the implant 200 can be rotated such that the contralateral iliac portion 230 is rotated into the contralateral common iliac artery 140. In some embodiments, the remainder of the sheath is then removed and the filler pocket 280 is completely filled with the filler material, as illustrated in FIG. 5.

Figure 5:
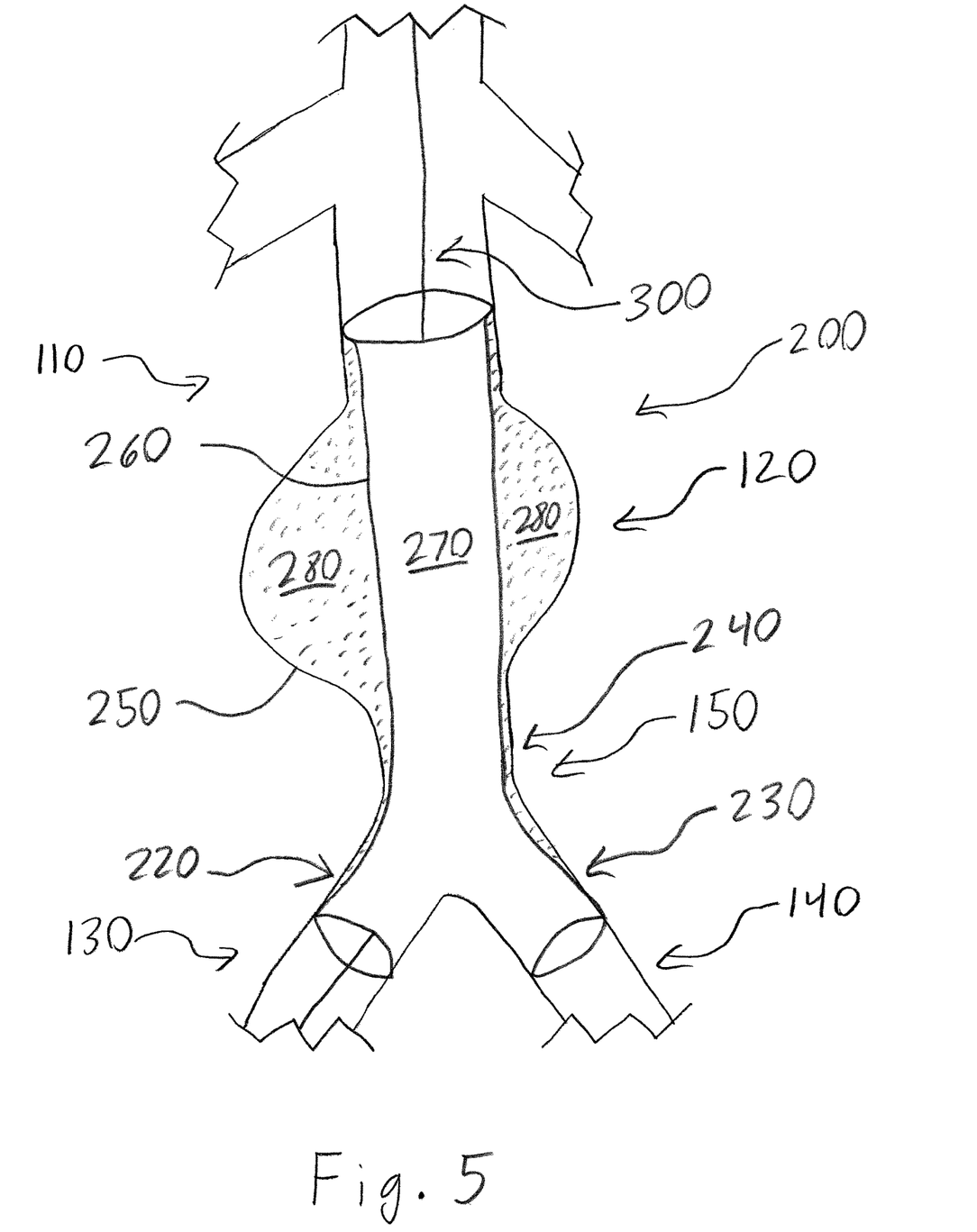
FIG. 5 illustrates a cross section of the implant of FIG. 2 completely filled with filler material and deployed within an abdominal aorta including an aneurysm.

FIG. 5 illustrates a cross section of the implant of FIG. 2 completely filled with filler material and deployed within an abdominal aorta including an aneurysm. Once implanted, the implant position and absence of leak around the device can be checked with an angiogram and the filler material is activated and solidifies within the implant 200. The implant 200 then fills the aneurysm 120 as illustrated in FIG. 5 and the shape of the implant 200 maintained by the solidified filler material can hold the implant 200 in place. In some embodiments the outer wall 250 can be coated with a first bioactive agent, such as an agent to promote hemostasis, such as thrombin, chitin, chitosan, fibrin, collagen, or a combination thereof, for example. In some embodiments, the inner wall 260 of the implant can be coated with one or more anticoagulant agents, such as heparin, hirudin, or enoxaparin for example, to minimize the chance of intravascular thrombosis. In some embodiments, the inner wall 260 of the implant could be coated with an immunosuppressant or antiproliferative agent, such as paclitaxel (Taxol), rapamycin (Sirolimus), zotarolimus, or tacrolimus.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention.

The invention claimed is:

1. A method for manufacturing an aortic aneurysm endograft, comprising steps of:
   creating a computer tomography (CT) angiography image, in digital imaging and communications in medicine (DICOM) format, of a target aneurysm to measure:
   a size and a shape in a specific patient,
   dimensions of an aneurysmal aorta having aneurysmal dilatation of an aorta and iliac arteries, and
   a position of adjacent side branches, including at least one of renal arteries, internal iliac arteries, a superior mesenteric artery, a celiac axis, a left subclavian artery, a left common carotid artery, and a brachiocephalic trunk;
   converting said image to computer assisted design (CAD) software format;
   operating a 3 dimensional (3D) printer to manufacture two mandrels, wherein:
   both of the two mandrels are printed from a heat resistant material;
   the mandrels are printed in a positive format or a negative format to accommodate respective planned balloon manufacturing techniques;
   the two mandrels comprising a first mandrel and a second mandrel;
   using said mandrels to create an inner wall and an outer wall of the endograft comprising:
   the first mandrel formed in the size and the shape of a lumen of a non-aneurysmal aorta in the specific patient;
   the second mandrel formed using the image in CAD format and comprising the size and the shape of the aorta having the aneurysmal dilatation in the specific patient;
   subjecting the first mandrel to a first of the respective planned balloon manufacturing techniques to form the inner wall of the endograft on the first mandrel;
   subjecting the second mandrel to a second of the respective planned balloon manufacturing techniques to form the outer wall of the endograft on the second mandrel the size;
   securing together the inner wall and the outer wall at their proximal and distal ends to create a space between the inner wall and the outer wall;
   post-printing a surface modification on the first mandrel and/or the second mandrel when a respective surface thereof has porosity or irregularity, resulting from the 3D printing, the post-printing step comprising polishing or coating the first and/or second mandrel having the porosity or irregularity with a heat resistant sealer.

2. The method of claim 1, further comprising:
the inner wall is manufactured from non-compliant material comprising nylon or polyester and the first planned balloon manufacturing technique comprises injection molding or blow molding;
the outer wall is manufactured from a compliant material, to accommodate an irregular shape of an aneurysm wall, the compliant material comprising silicone or polyurethane, the second planned balloon manufacturing technique comprising dip molding, blow molding, or injection molding.

3. The method of claim 1, further comprising:
a filing tube is attached to the outer wall of the endograft to enable filling the space between the inner wall and the outer wall of the endograft, the filling of the space resulting in full deployment of the endograft, the filling tube being detachable in its midsection forming a proximal part and a distal part;
a plastic flap covering an entry point of the filling tube into the space, where the flap serves as a one way valve to prevent back flow of a filling material from the space back into the filling tube.

4. The method of claim 3, further comprising:
an additional one way valve within the filling tube for additional security in preventing the back flow.

5. The method of claim 4, further comprising:
the filling tube is detachable distal to the one way valve to allow removal after injecting the filling material.

6. The method of claim 3, further comprising:
an inner surface of the inner wall is coated with an anticoagulant, to minimize the risk of blood clotting within the endograft;
an outer surface of the outer wall is coated with a procoagulant, to promote closure of side branches thus minimizing the possibility of development of endoleaks.

7. The method of claim 6, further comprising:
sterilizing all surfaces of the endograft.

8. The method of claim 7, further comprising:
folding the endograft into a delivery catheter, wherein the delivery catheter comprises
a 0.035" inner lumen to accommodate a guide wire and an outer sheath which contains the folded endograft and
positioning the endograft within the lumen of the aorta,
after the positioning of the endograft within the lumen, pulling the outer sheath back and out of a body of the specific patient to allow for inflation of the space of the endograft.

9. The method of claim 8, further comprising:
after completing the filling of the space, removing the distal part of the filling tube while the proximal part remains trapped between the aorta and the endograft, and
removing the guide wire.

10. The method according to claim 6, further comprising:
the anticoagulant is heparin and the procoagulant is thrombin.

11. The method of claim 3, further comprising:
the filling of the space between the inner wall and the outer wall of the endograft comprises the following steps:
injecting a first component of the filling material to inflate and self-position the endograft within a body of the aneurysm, said first component comprising a liquid thereby allowing for deflation and repositioning of the endograft;

positioning the endograft by positioning right and left iliac limbs of the endograft in the right and left iliac arteries, respectively, in order to anatomically align the endograft;

after the step of positioning the endograft, a second component of the filling material is injected into the space, wherein the first and the second components chemically react to solidify into a semi rigid state, said semi rigid state maintaining a shape of the endograft, thereby securing the position of the endograft within the aneurysm while also allowing for minimal deformation to accommodate physiological movements of vasculature, including changes in shape of the target aneurysm over time.

12. The method of claim 1, further comprising:

the space being a watertight cavity between the first wall and the second wall.

13. The method of claim 12, further comprising:

testing the endograft for complete sealing and for all potential leaks being eliminated.

* * * * *